United States Patent [19]
Paciorek

[11] 4,200,721
[45] Apr. 29, 1980

[54] HEAT RESISTANT POLYMERS OF OXIDIZED STYRYLPHOSPHINE

[76] Inventor: James C. Fletcher, Administrator of the National Aeronautics and Space Administration, with respect to an invention of Kazimiera J. L. Paciorek, Corona Del Mar, Calif.

[21] Appl. No.: 907,479

[22] Filed: May 19, 1978

Related U.S. Application Data

[62] Division of Ser. No. 706,424, Jul. 19, 1976, Pat. No. 4,092,466.

[51] Int. Cl.$^2$ .............. C08F 26/00; C08C 19/22; C08F 30/02; C08F 230/02
[52] U.S. Cl. .................... 526/261; 525/326; 525/336; 525/340; 525/374; 525/375; 526/275; 526/276; 526/278; 260/DIG. 24; 528/481
[58] Field of Search .............. 526/13, 23, 27, 49, 526/50, 261, 275, 276

[56] References Cited

U.S. PATENT DOCUMENTS

| | | |
|---|---|---|
| 3,725,365 | 4/1973 | McKinley et al. ............ 526/278 |
| 3,853,794 | 12/1974 | Reynard et al. ............. 526/168 |
| 3,948,820 | 4/1976 | Mentor et al. ............. 526/276 |

*Primary Examiner*—Joseph L. Schofer
*Assistant Examiner*—Herbert J. Lilling
*Attorney, Agent, or Firm*—Carl O. McClenny; John R. Manning; Marvin F. Matthews

[57] ABSTRACT

Homopolymers, copolymers and terpolymers of a styrene based monomer are prepared by:

(1) polymerizing at least one oxidized styrylphosphine monomer selected from the group of:
$(C_6H_5)_2P(O)N=P(C_6H_5)_2C_6H_4CH=CH_2$,
$(C_6H_5O)_2P(O)N=P(C_6H_5)_2C_6H_4CH=CH_2$,
$(C_6H_5)_2C_3N_3N=P(C_6H_5)_2C_6H_4CH=CH_2$ and
$(C_6H_5)C_3N_3[N=P(C_6H_5)_2C_6H_4CH=CH_2]_2$; or (2) polymerizing p-diphenylphosphinestyrene and then oxidizing said polymerized p-diphenylphosphinestyrene monomer with an organoazide selected from the group of $(C_6H_5)_2P(O)N_3$, $(C_6H_5O)_2P(O)N_3$, $(C_6H_5)_2C_3N_3(N_3)$ and $C_6H_5C_3N_3(N_3)_2$. Copolymers can also be prepared by copolymerizing styrene with at least one oxidized styrylphosphine monomer selected from the group of:
$(C_6H_5)_2P(O)N=P(C_6H_5)_2C_6H_4CH=CH_2$,
$(C_6H_5O)_2P(O)N=P(C_6H_5)_2C_6H_4CH=CH_2$,
$(C_6H_5)_2C_3N_3N=P(C_6H_5)_2C_6H_4CH=CH_2$ and
$(C_6H_5)C_3N_3[N=P(C_6H_5)_2C_6H_4CH=CH_2]_2$.

15 Claims, No Drawings

HEAT RESISTANT POLYMERS OF OXIDIZED STYRYLPHOSPHINE

ORIGIN OF THE INVENTION

The invention described herein was made in the performance of work under a NASA contract and subject to the provisions of Section 305 of the National Aeronautics and Space Act of 1958, Public Law 85-568(72 stat 435; 42 USC 2457).

This is a division, of application Ser. No. 706,424, filed July 19, 1976, now U.S. Pat. No. 4,092,466.

BACKGROUND OF THE INVENTION

1. Field of the Invention

The present invention relates to flame-resistant, non-toxic vinyl polymers which contain phosphazene groups. The polymers of the present invention do not emit any toxic or corrosive products when they are oxidatively degraded.

2. Description of the Prior Art

Presently, there are available a number of flame resistant materials and materials combinations. The vast majority of these, however, produce unacceptably large amounts of toxic and corrosive substances when subjected to oxidative thermal decomposition even in the absence of a flame. The toxic product formation is as great a hazard as a fire itself in any confined location and is particularly dangerous in space capsules, aircraft, or submarines, where egress or ventilation cannot be readily accomplished. The applicability of the few polymeric compositions which are flame resistant and do not form toxic degradation products, on the other hand, is limited because of cost, often poor processibility, and the fact that they do not lend themselves to modifications to improve deficiencies in physical or mechanical characteristics. These materials are based on highly condensed aromatic structures which during oxidative thermal decomposition form chars in high yields, and thus, release combustible decomposition products at too low a rate to support a flame.

All other flame resistant compositions derive this property from the presence of elements, which are known to act as flame retardants. These are elements of the third, fifth, and seventh main groups of the periodic table, specifically boron, nitrogen, phosphorus, antimony, and the halogens. Of these, only nitrogen, phosphorus, and the halogens are directly bonded in or to the polymer backbone. Boron and antimony normally are physically admixed with the flame resistant compositions, the former usually as a salt of boric acid, the latter either as its oxide or oxychloride. Yet internal bonding is preferable to admixture since additives are subject to removal by physical and chemical processes such as abrasion and washing.

The halogenated flame resistant materials such as polytetrafluoroethylene, copolymers of perfluoropropene and vinylidene fluoride, or polyvinylchloride contain the flame retardant bonded to the polymer backbone. Some of these materials exhibit very good flame resistance and have other desirable characteristics such as good mechanical properties and good processibility. However, these materials upon oxidative thermal decomposition produce copious quantities of highly toxic and corrosive gases. Moreover, the thermal decomposition process can take place long before flame temperatures are reached. Polyvinylchloride, for example, was found to lose practically all of the chlorine present (56.7%) in the form of toxic and corrosive hydrogen chloride at about 280° C. leaving a residue which was combusted by excess air in a strongly exothermic reaction (Boettner et al; Organic Coatings and Plastics Chemistry, Preprints, 28, No. 1, 311, April 1968). Polytetrafluoroethylene (Teflon), when exposed to elevated temperature in the presence of air, was shown by K. L. Paciorek et al, Final Report, Part I, Contract NASW-1921, August 1970; CR 114357 and K. L. Paciorek et al, Final Report, Part II, Contract NASW-1921, June 1971 to form carbonyl fluoride, which is hydrolyzed to toxic hydrogen fluoride and carbon dioxide, if water is also present. Fluorinated polymers, which also contain hydrogen, e.g., the copolymer of perfluoropropene and vinylidene fluoride (Viton, Fluorel) release hydrogen fluoride directly if not judiciously compounded. One of the reasons for this behavior is that halogens can be present in a polymer only as singly bonded moieties, and consequently cannot be incorporated into the normally more stable polymer backbone. Accordingly, the fire retarding element can be removed from the material by such simple reactions as dehydrohalogenation. This type of action is unlikely to occur in the case of an element which is either multiply bonded in the backbone or which is a part of an aromatic structure, thus capable of charring without volatilization upon exposure to a flame or elevated temperatures.

The remaining two of the above enumerated elements known to act as flame retardants are nitrogen and phosphorus, both of which are multivalent, thus can be incorporated in a polymer backbone, and are capable of multibonding. The flame retarding capability of triazine type compounds, and especially of phosphorus-nitrogen combinations, has been amply documented. U.S. Pat. No. 2,514,268 (1950); Brit. Patent No. 638,434 (1950); R. C. Nametz, Ind. Engin. Chem., 59, 99 (1967); G. C. Tesoro et al, 155th ACS Meeting, Organic Coatings and Plastics Chemistry, Preprints, 28, No. 1, 243, April 1968; H. R. Allcock, C&EN, Apr. 22, 1968, 68–81, and C. E. Miles et al, 155th ACS Meeting, Organic Coatings and Plastics Chemistry, Preprints, 28, No. 1, 237, April 1968. The exact nature of their action as flame retardants either alone or in combination is not known. Either one of the elements would be expected to interfere in the free radical chain reactions propagating the flames. More importantly, however, both are known to form strong chars and accordingly do not contribute fuel to the flame. Such chars, in addition, insulate thermally the lower layers of the polymers thus inhibiting pyrolysis, and depress or prevent the access of oxygen to the subsurface. Phosphorus, when contained in an aromatic structure or when substituted by aromatic moieties such as phenyl groups, forms mechanically particularly strong chars, which have been shown to exhibit the above properties.

Flame-resistant polymers containing phosphazene repeating units in the polymer backbone are known, see for example U.S. Pat. Nos. 3,702,837, 3,888,799 and 3,896,058. However, these polymers lack the mechanical properties and good processability possessed by vinyl polymers such as polystyrene. As a result, these polymers have a limited field of use.

Accordingly, there exists a need for flame resistant polymers whose degradation products are both non-toxic and non-corrosive which possesses mechanical and processing properties similar to those of known vinyl polymers.

SUMMARY OF THE INVENTION

It is an object of the present to prepare vinyl polymers which are flame-resistant and whose degradation products are non-toxic and non-corrosive.

It is another object of the present invention to provide a process for preparing flame-resistant homopolymers, copolymers and terpolymers.

Still another object of the present invention is to provide a flame-resistant, non-toxic polymer which may safely be used in confined locations where there is inadequate ventilation.

Briefly, these objects and other objects of the present invention as hereinafter will become more readily apparent can be attained by polymers prepared by polymerizing compounds having the formula:

$$R-N=P\ (C_6H_5)_2\ (C_6H_4)\ CH=CH_2$$

wherein R is an organic moiety selected from the group of:

$(C_6H_5)_2\ P(O)-, (C_6H_5O)_2P(O)-, (C_6H_5)_2\ C_3N_3-$, mixtures thereof or by polymerizing a compound having the formula $C_6H_5C_3N_3[N=P(C_6H_5)_2(C_6H_4)CH=CH_2]_2$; or by reacting a polymer of the formula:

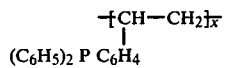

with an organic azide selected from the group of $(C_6H_5)_2P(O)N_3$, $(C_6H_5O)_2P(O)N_3$, $(C_6H_5)_2(C_3N_3)(N_3)$, $(C_6N_5)\ C_3N_3(N_3)_2$ and mixtures thereof. By judicious choice of the reactants homopolymers, copolymers and terpolymers can be prepared by polymerizing mixtures of the above azido oxidized styrylphosphine monomers and by polymerizing one or more of these monomers with a vinyl monomer such as styrene. Alternatively, the interpolymer can be prepared by first polymerizing diphenyl-p-styryl phosphine either alone or with another vinyl monomer to prepare a polymer. The resulting polymer is then reacted with an organo azide to introduce phosphazene groups into the resultant polymers.

The polymers of the present invention can be molded into shaped articles and films using conventional techniques.

DETAILED DESCRIPTION OF THE PREFERRED EMBODIMENTS

The polymers of the present invention are vinyl based polymers characterized by containing pendant radicals containing phosphazene groups. The polymers can be prepared by two techniques in which the first route involves the polymerization of at least one organoazide oxidized styrylphosphine monomer, and the second route involves the preliminary polymerization of styrylphosphine monomer and subsequent oxidation of the pendant phosphine moieties in the polymer with at least one organoazide. In the context of the present invention the term styrylphosphine monomer not only includes the ortho, meta and para isomers of styryldiphenylphosphine, but also includes other vinylaromatic diphenyl phosphines such as vinylnaphthyldiphenylphosphine. Furthermore, each aromatic residue in the monomer can be substituted by one or more substituents such as alkyl, preferably lower alkyl of one to six carbon atoms, nitro, halo such as chloro, bromo and iodo, and the like.

In the first route, the appropriate monomer(s) is prepared by oxidatively reacting a styrylphosphine compound with an organoazide. The type of organoazide selected for the reaction is not critical. Suitable organoazides include diphenylphosphinylazide, $(C_6H_5)_2P(O)N_3$; diphenylphosphorylazide, $(C_6H_5O)_2P(O)N_3$; 2-azido-4,6-diphenyl-5-triazine, $(C_6H_5)_2C_3N_3(N_3)$; 2,4-diazido-6-phenyl-s-triazine, $(C_6H_5)C_3N_3(N_3)_2$, trimethylsilylazide, triphenylsilylazide and phenylazide. The reaction of the styrylphosphine with the organoazide results in the oxidation of the trivalent phosphorous atom to the pentavalent state in the form of an unsaturated P=N linkage known as a phosphazene group.

The basic styrylphosphine monomer of the present invention can be prepared by any convenient and acceptable technique. In one embodiment styrylphosphine can be prepared by synthesizing a reactive Grignard agent of chlorostyrene. The Grignard agent is then reacted with diphenyl halophosphine to complete the preparation. In another embodiment an active lithium intermediate can be prepared by reacting the chlorostyrene with an organo lithium compound such as butyllithium, and then reacting the reagent prepared with diphenylhalophosphine.

The oxidized monomer of the present invention can be prepared by mixing stoichiometric quantities of organoazide and styrylphosphine in a solvent. Suitable solvents include dialkyl ethers such as diethyl ether, dipropyl ether and the like; tetrahydrofuran, acetonitrile; aromatic hydrocarbons such as benzene, xylene, toluene and the like and halohydrocarbons such as chloroform, methylenechloride and the like. The reaction temperature is not critical, but usually ranges from 0° C. to ambient temperature depending on the activity of the azide. Slow reacting azides may require temperatures as high as refluxing temperatures. The reaction pressure also is not critical. During the course of the reaction nitrogen is evolved as evidence of the destruction of the azido compound. The desired oxidized monomer can then be obtained by any suitable precipitation or solvent removal technique. In some instances oxidation of styrylphosphine monomer results directly in the formation of a homopolymer without the isolation of the oxidized monomer. Thus, when styrylphosphine is reacted with diphenylphosphinyl azide, a polymeric material of the formula:

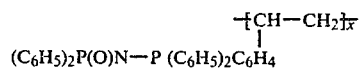

is obtained, and the oxidized monomer, $$(C_6H_5)_2P(O)N=P(C_6H_5)_2C_6H_4CH=CH_2$$

is not isolated. Diphenylphosphoryl azide when reacted with styrylphosphine also results in the formation of some polymer material, however, not to the extent obtained with diphenylphosphinylazide. Reaction of styrylphosphine with the other azide oxidizing agents does not result in the formation of polymer. Only the desired oxidized monomer is obtained. It thus appears that there is a relationship between the ease or rate of oxidation of styrylphosphine by an azide and the ability of the azide to function as a polymerization catalyst. The triazene azides, which promote the oxidation reaction very quickly, do not seem to promote the polymerization reaction. It may be that during oxidation a transition state exists which activates the double bond of styrylphosphine so that it undergoes polymerization.

The polymerization reaction of the invention as it relates either to the polymerization of an oxidized styrylphosphine monomer or to the polymerization of styrylphosphine monomer which is later oxidized with at least one organoazide, can be conducted by bulk polymerization techniques. An alternative technique can be the homopolymerization or copolymerization of the styrylphosphine monomer in an organic solvent such as benzene or toluene, with a radical initiator such as 2,2'-azobis-(2-methylpropionitrile). This reaction is usually conducted under an inert atmosphere of nitrogen argon or the like at 50°–100° C. for 4–200 hours. In conducting the bulk polymerization of either the oxidized or unoxidized styrylphosphine monomer, it is necessary to achieve a polymer product having as high a molecular weight as possible in order to obtain a polymeric material having satisfactory molding and film forming characteristics as well as a satisfactory melting or softening range. While the molecular weight can widely vary the molecular weights of the polystyrylphosphine usually ranges from 10,000 to 100,000. These values, as determined with an osmometer, are number average molecular weights. Any convenient method can be used for the bulk polymerization of both oxidized and unoxidized styrylphosphine monomer. In one embodiment of the bulk polymerization process, a desired quantity of a monomer or desired quantities of more than one monomer are sealed in an enclosed reactor and heated to 60° C. to 250° C., preferably 60° C. to 250° C. to effect polymerization. If necessary, a radical initiator such as 2,2'-azobis(2-methylpropionitrile) can be used either with or without the presence of an organic solvent. The reaction is normally conducted from ⅓ to 288 hours, preferably 0.5 to 24 hours. In many instances, longer reaction times can be used at lower temperatures in the indicated range. Once the reaction is complete, the reaction residue is treated with an appropriate solvent to remove soluble polymer products therefrom. Suitable solvents for the extraction include halohydrocarbons such as chloroform and the like. The precipitated polymer is then isolated by any convenient technique such as filtration and then dried.

In any embodiment of the bulk polymerization procedure, a desired quantity of monomer or desired quantities of more than one monomer are placed in an evacuated reactor. After evacuation of the reactor, usually a glass ampoule, to a suitable pressure of about $10^{-3}$ mm, the ampoule is then heated to 60° C. to 250° C., preferably 150° C. to 230° C. to effect polymerization over a time period of ⅓ to 288 hours, preferably 0.5 to 24 hours. Instead of conducting the reaction under a vacuum the reaction can be conducted under an inert atmosphere such as nitrogen, or the like. After the reaction is complete, the desired polymer product can be isolated as described supra.

By the use of a suitable bulk polymerization procedure, an oxidized styrylphosphine monomer such as $(C_6H_5O)_2P(O)N=P(C_6H_5)_2C_6H_4CH=CH_2$, $(C_6H_5O)_2P(C_6H_5)_2C_6H_4CH=CH_2$,

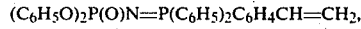

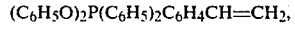

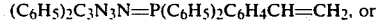

can be polymerized to yield homopolymers having a molecular weight range of 10,000 to 100,000. The polymerization reactions for the homopolymers can be conducted at a temperature ranging from 130° C. to 230° C. For the homopolymerization of $(C_6H_5O)_2P(O)N=P(C_6H_5)_2C_6H_4CH=CH_2$, the polymerization temperature preferably ranges from 150° C. to 160° C. If the polymerization temperature is elevated to about 230° C., cross-linking of the polymer product obtained occurs. Polymeric material having a molecular weight range of 50,000 to greater than 100,000 can be obtained. The homopolymer is oxidatively stable up to temperatures of about 275° C. For the homopolymerization of $(C_6H_5)C_3N_3[N=P(C_6H_5)_2C_6H_4CH=CH_2]_2$, the polymerization temperature preferably ranges from 130° C. to 160° C. and always provides a cross-linked material because of the difunctionality of the monomer. If the reaction is conducted at a temperature of about 160° C., the resulting product is mostly chloroform insoluble indicating a highly cross-linked polymer product. The polymer product obtained, when heated, starts to thermally decompose at about 300° C. However, the char yield upon decomposition stabilizes at 41% at about 550° C., and does not seem to decrease further at temperatures up to 610° C.

Copolymeric materials can be prepared by reacting two of the oxidized styrylphosphine monomers of the present invention in any suitable bulk polymerization procedure at a temperature ranging from 150° C. to 235° C. for 0.5 to 5.0 hours at mole ratios ranging from 1:1 to 1:10. Included within the scope of the copolymerization reaction are both styrylphosphine monomer and styrene. From analysis of the soluble fractions of the polymers, the molecular weight ranges from 15,000 to 34,000.

In one embodiment of the copolymerization aspect of the invention diphenyl-p-styrylphosphine can be bulk polymerized with

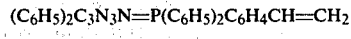

in any suitable relative amounts to produce a copolymer of good thermal stability. Usually, however, equimolar quantities of reacting monomers are used. In another embodiment of the copolymerization procedure appropriate quantities of

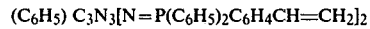

can be reacted with

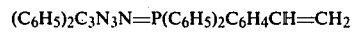

usually in a mole ratio of 1:20, to form a polymeric residue containing both chloroform soluble and insoluble polymers. Both insolube and soluble portions of the copolymer can be used in the preparation of molded articles.

Terpolymeric polymeric materials can also be prepared by coreacting three oxidized styrylphosphine monomers by any suitable bulk polymerization procedure at a temperature ranging from 165° C. to 230° C. The reacting monomers can be polymerized in any appropriate quantities. However, when the difunctional monomer $(C_6H_5)C_3N_3[N=P(C_6H_4)_2C_6H_4CH=CH_2]_2$, is used as a reactant, it should not be used in proportional amounts greater than 10 mole %, i.e., no greater than a ratio of 1:10 relative to the other monomers. Difunctional monomer containng polymers can be molded into transparent discs at 350° F. and a pressure of about 750 lbs. Since the polymer product obtained when the difunctional monomer is used as a reactant, is can be prepared by reacting diphenylphosphoryl azide with polystyrylphosphine. The product prepared by the oxidation of preformed polystyrylphosphine can be readily molded to form articles. Moreover, polymer films can be cast from solution onto an aluminum surface. It is believed that partially oxidized polymer

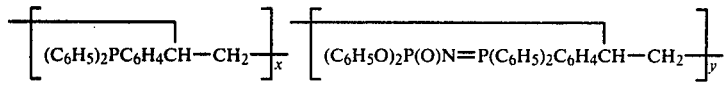

solvent insoluble, molecular weights can not be determined. However, the minimum molecular weight is believed to be about 20,000. In a preferred embodiment should be also amenable to fabrication of useful articles; however, this type of material would be expected to undergo oxidation to the oxide

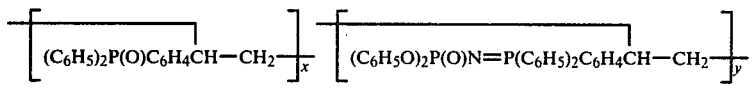

of the present invention terpolymer can be prepared by reacting 50 to 90 mole % of $(C_6H_5O)_2P(O)N=P(C_6H_5)_2C_6H_4CH=CH_2$, 36 to 15 mole percent of $(C_6H_5)_2C_3N_3N=P(C_6H_5)_2C_6H_4CH=CH_2$ and 10 to 2 mole percent of $(C_6H_5)C_3N_3[N=P(C_6H_5)_2C_6H_4CH=CH_2]_2$.

Polystyrylphosphine materials of the present invention can also be prepared by a second route as mentioned earlier by first bulk polymerizing styrylphosphine. Essentially the same time and temperature conditions as described earlier for the bulk polymerization of the oxidized styrylphosphine can be employed for the bulk polymerization of styrylphosphine. The molecular weight range for the polymerized product generally ranges from 10,000 to 67,000. The polystyrylphosphine once obtained, is then oxidatively reacted by any suitable procedure with an appropriate organoazide to form the desired phosphazene homopolymer or is oxidatively reacted with two or more organoazides to form appropriate copolymers and terpolymers. The oxidation reaction is conducted in an organic solvent wherein suitable solvents include tetrahydrofuran, diglyme, benzene, toluene, chloroform and the like. Reaction temperature is not critical and is usually ambient temperature. Normally, the amount of azide employed is that amount sufficient to react with all of the phosphine units in the polymer. Thus, for instance, a homopolymer of the formula

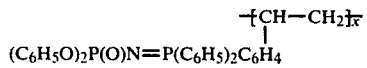

Copolymers can be prepared by reacting the preformed polystyrylphosphine with two organoazides in appropriate quantities in much the same manner polystyrylphosphine is reacted with only one organoazide. When two organoazides are reacted with the preformed polystyrylphosphine, they can be reacted in any relative amounts either simultaneously or consecutively. Thus, in a preferred embodiment of this aspect of the invention, from 50 to 90 mole percent of

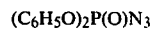

is reacted with a unit amount of styrylphosphine polymer followed by 50 to 10 mole % of

In a manner similar to that used above for the preparation of copolymers, terpolymers can be prepared by reacting the desired amounts of three organoazides with a unit amount of polystyrylphosphine. In the terpolymers if monofunctional azides are employed, these can be used in equal mole percent or any other percentages depending on the desired properties of the final polymer. All of the three azides can be added simultaneously. However, if a difunctional azide is employed to yield a crosslinked product, it has to be added after the monoazides have reacted to avoid intramolecular reactions, i.e., joining of adjacent sites on the same polymer chain. An especially useful terpolymer which is amenable to molding and film casting and which has high molecular weight is high melting and yet soluble, can be prepared as follows:

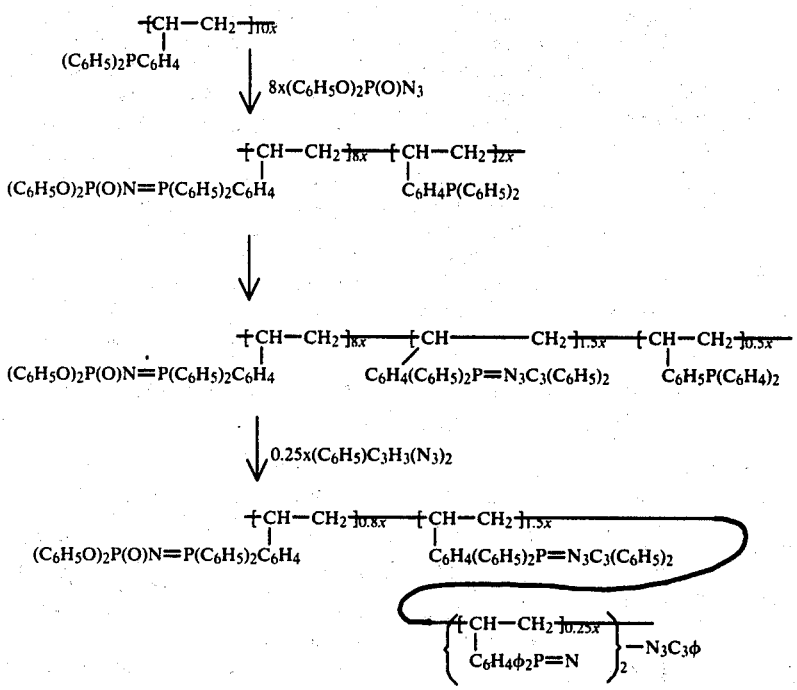

(The above reaction sequence is not to be interpreted as meaning that block copolymers are formed by this procedure.)

In another aspect of the invention phosphazene group containing styryl polymers can be obtained by copolymerizing styrene with the reactive monomer(s) in either of the polymerization procedures of the invention. Other suitable comonomers include those which are amenable to copolymerzation with styrene such as butadiene. Thus, when an oxidized styrylphosphine monomer or more than one oxidized styrylphosphine monomer is reacted with styrene, from 20 to 95 mole % of styrene can be reacted with 80 to 5 mole % of oxidized styrylphosphine monomer(s). In the situations where the object polymers are prepared by oxidizing the pendant phosphine groups of performed styrylphosphine polymers, from 20 to 95 mole % of styrene can be reacted with from 80 to 5 mole % of styrylphosphine monomer. Preferred embodiments of copolymers derived from the polymerization of styrene with an oxidized styrylphosphine monomer include a copolymer having the formula:

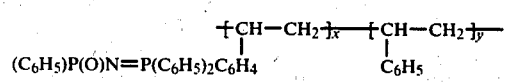

wherein X is 50–10 mole percent and y is 50–90 mole percent; and a copolymer of the formula:

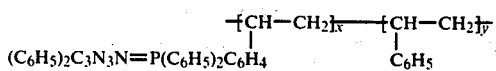

wherein x is 50–10 mole percent and y is 50–90 mole percent.

According to thermal gravimetric analysis data, the homopolymers, copolymers and terpolymers of the invention are thermally stable. Some of the homopolymers appear to be thermally stable up to 350° C. In fact, under conditions which cause polystyrene to explode, i.e. a temperature of 540° C. under a dynamic flow of oxygen preheated to 540° C., a Nomex cloth impregnated with 32% of $+(C_6H_5)_2 P(O)N=P(C_6H_5)_2C_6H_4CH=CH_2]_x$ gave an 86% residue.

The phosphazene group containing styryl polymers of the present invention are characterized by having satisfactory molding and film forming characteristics as well as being non-toxic when thermally decomposed. The polymers are self-extinguishing when ignited in air. Moreover, the polymeric materials are heat resistant and possess higher char yields than styrene. The polymeric materials of the present invention can be used in the manufacture of components of systems such as space crafts, air crafts, and the like from which egress in the presence of fire is difficult or impossible. In addition co- and terpolymers obtained by copolymerization of the styrylphosphine oxidized monomer with other conventional monomers can be employed for the same applications, mainly as structural materials, where styrene copolymers are used with the advantage that the presence of the chemically bonded phosphorus will render these materials more flame resistant than is the case usually with styrene based compositions.

Having generally described this invention, a further understanding can be obtained by reference to certain specific examples which are provided herein for purposes of illustration only and are not intended to be limiting unless otherwise specified.

I. PREPARATION OF ORGANOAZIDE REACTANTS

All solvents used were reagent grade and were dried and distilled prior to use. All operations involving moisture or air sensitive materials were carried out either in an inert atmosphere enclosure (Vacuum Atmospheres Model HE-93B), under nitrogen by-pass, or in sealed ampoules. The commercially available starting materials were usually purified by distillation, crystallization, or other appropriate means. All molecular weights were determined using a Mechrolab Osmometer Model 302.

The melting points of all solid monomers were determined in nitrogen filled sealed melting point capillaries, softening and melting points of the polymers were obtained using a Fisher-Johns apparatus.

EXAMPLE 1

PREPARATION OF 2-CHLORO-4,6-DIPHENYL-S-TRIAZINE

The procedure used was based on the method of Jones et al, AD 229453, September 1959. A stirred mixture of magnesium turnings (24.3 g, 0.935 mol) and a crystal of iodine in ether (150 ml), was added a solution of bromobenzene (155.3 g, 0.985 mol) in ether (100 ml) under a nitrogen atmosphere over a period of 3.75 hr at such a rate as to maintain a gentle reflux. Thereafter, the mixture was refluxed for 2.5 hr. The Grignard reagent thus prepared was then cooled and transferred to an addition funnel and added with stirring to a solution of cyanuric chloride (70 g, 0.38 mol) in benzene (500 ml) at 4°–15° C. (ice bath cooling) over a period of 1.25 hr. After stirring overnight the mixture was refluxed for 4 hr, cooled, and filtered. The filtrate was evaporated to dryness using a Rinco evaporator yielding 136.5 g of crude product mixture. This mixture was distilled in vacuo at 0.007 mm. The desired product, bp 140°–152° C., 63.5 g(62% yield), was crystallized three times from heptane yielding pure 2-chloro-4,6-diphenyl-s-triazine, 46.1 g (45% yield), mp 136°–138° C.

EXAMPLE 2

PREPARATION OF 2-AZIDO-4,6-DIPHENYL-S-TRIAZINE

A suspension of 2-chloro-4,6-diphenyl-s-triazine (30 g, 0.112 mol), sodium azide (12.86 g, 0.199 mol) and lithium azide (1.25 g, 0.025 mol) in acetonitrile (550 ml) was stirred at room temperature for 11 days. After filtration, the filtrate on evaporation yielded 6.9 g of 2-azido-4,6-diphenyl-s-triazine, mp 115°–117° C. The residue on extraction with hot heptane, followed by crystallization from heptane, gave an additional 20 g quantity having a mp of 114°–116° C. bringing the total yield of 2-azido-4,6-diphenyl-s-triazine to 26.9 g (88% yield). The melting point and infrared spectrum were identical with that of an authentic sample.

EXAMPLE 3

PREPARATION OF 2, 4-DICHLORO-6-PHENYL-S-TRIAZINE

This compound was prepared via a two-step reaction using a combination of two literature procedures. A mixture of 2,4-diamino-6-phenyl-s-trazine (150 g, 0.802 mol) and 90% sulfuric acid (600 ml) was heated with stirring in an oil both maintained at 105°–124° C. for 20.5 hr. After cooling to 70° C., the mixture was poured over 5000 ml crushed ice. Upon standing overnight in the refrigerator, the solution deposited a white solid which was collected, washed with water (3000 ml) and dried to give 128.1 g, (84% yield) of 2,4-dihydroxy-6-phenyl-s-trazine, mp 290°–294° C. (dec.); lit. 289°–290° C. (dec). (Belgian Patent 634,399 (1964); Chem. Abstracts, 61, 671(1964)).

To a stirred mixture of 2,4-dihydroxy-6-phenyl-s-triazine (45 g, 0.238 mol) and thionyl chloride (250 ml) was added dropwise under anhydrous conditions dimethylformamide (50 ml) over a period of 10 min. Thereafter, the reaction mixture was heated with stirring in an oil bath maintained at 70°–75° C. for 3.5 hr. After cooling to ambient conditions, the excess thionyl chloride was removed in vacuo. The resulting solid was stirred with an ice-water mixture (2 l) at 15°–20° C. for 2 hr. The solid was then collected by suction filtration, washed with water (800 ml) and dried in vacuo to give 44.5 g (83.3% yield) of crude product, which was extracted with boiling heptane. Upon cooling the heptane extract deposited 2,4-dichloro-6-phenyl-s-triazine in several crops. Total amount of product was 39.5 g, (73% yield), mp 117.5°–120° C.; mp 121° C. (H. Albers et al, German Patent No. 1,178,052; Chemical Abstracts, 61, 16080 (1964)); mp 120°–120.5° C. (R. E. Jones et al, AD 229453, Sept. 1959).

EXAMPLE 4

2,4-DIAZIDO-6-PHENYL-S-TRIAZINE

A mixture (prepared in a inert atmosphere enclosure) of sodium azide (19.57 g, 0.3 mol), lithium azide (1.0 g, 0.0204 mol), 2, 4-dichloro-6-phenyl-s-trazine (23.0 g, 0.102 mol) and acetonitrile (400 ml) was stirred at ambient conditions under a nitrogen atmosphere for 160 hr. Filtration gave 33.5 g of insoluble materials, whereas evaporation of the filtrate using a rotary evaporator afforded 9.2 g of material which was crystallized from heptane yielding 8.0 g of 2,4-diazido-6-phenyl-s-triazine, mp 130°–131° C. The insoluble material was extracted with boiling heptane which upon partial evaporation and cooling, afforded 12.8 g of material, mp 128.2°–131° C. Crystallization from heptane gave 12.2 g of 2,4-diazido-6-phenyl-s-triazine, mp 130°–132° C. Total yield of 2,4-diazido-6-phenyl-s-triazine was 20.2 g, (85.5% yield), mp 130°–132° C. The melting point and infrared spectrum were identical with that of the authentic sample.

EXAMPLE 5

PREPARATION OF TRIMETHYLSILYL AZIDE

The procedure employed was a variation [Paciorek et al, Inorg. Chem., 4, 1767 (1965)] of the method used by West and Thayer [R. West et al, J. Am. Chem. Soc., 84, 1763 (1962)]. Trimethylsilyl chloride was purified by distillation through a one meter spinning band column with 40% takeoff, bp 58°–59° C./763 mm. To trimethylsilyl chloride (215 g, 1.98 mol) in diglyme (352 ml) was added sodium azide (158 g, 2.42 mol). The resulting mixture was allowed to stand at room temperature with occasional shaking over a period of 8 days. Thereafter, the mixture was subjected to vacuum distillation at room temperature and the distillate (163.2 g, 74% yield) was collected in a Dry Ice trap. The crude trimethylsilyl azide was fractionated over a 1 meter spinning band column using 40% take-off, bp 97° C./760 mm.

EXAMPLE 6

PREPARATION OF DIPHENYLPHOSPHINYL CHLORIDE

Diphenylchlorophosphine (200 ml, 246 g, 1.12 mol) was heated with stirring at 100° C. and through this solution was bubbled gaseous oxygen dried by passing through towers filled with phosphorous pentoxide and Drierite. This process was performed over a period of 31 hr. The crude product was distilled in vacuo through a short Vigreaux column, the fraction with bp 164°-168° C. at 0.02 mm, 212 g (80.3% yield), exhibited an infrared spectrum identical to that of an authentic sample.

EXAMPLE 7

PREPARATION OF DIPHENYLPHOSPHINYL AZIDE

Following a previously [Paciorek et al, Inorg. Nucl. Chem. Letters, 2, 39 (1966)] developed procedure, diphenylphosphinyl chloride (14.87 g, 62.86 mmol) was introduced into a tube (in the inert atmosphere enclosure). Trimethylsilyl azide (10.45 g, 90.69 mmol) was then condensed onto this material on a vacuum line at liquid nitrogen temperature. The tube was sealed in vacuo and heated at 60° C. for 48 hr. Thereafter, it was cooled, opened to a vacuum system and the volatiles were collected in a liquid nitrogen trap (originally without pumping at room temperature, finally with pumping at 70° C.). The total time required to remove the volatiles (excess $(CH_3)_3SiN_3$ and the by-product $(CH_3)_3SiCl$) was 16 hr. A quantitative yield of pure diphenylphosphinyl azide was realized.

EXAMPLE 8

PREPARATION OF TRIPHENYLSILYL AZIDE

Following the method of Wiberg et al [Wiberg et al, Angew. Chem. Internat'l Ed.Engl., 1, 335 (1962)] in an inert atmosphere enclosure a solution of triphenylsilylchloride (73.9 g, 0.251 mol) in tetrahydrofuran (400 ml) was stirred with lithium azide (15.3 g, 0.312 mol) at room temperature over a period of 115 hr. After filtration, the solvent was removed in vacuo. The resulting white solid was boiled with heptane (350 ml), filtered hot and allowed to crystallize. Triphenylsilyl azide, 65.5 g (86.3% yield), mp 82°-84° C. was obtained. The melting point and infrared spectrum were identical with that of an authentic sample.

EXAMPLE 9

PREPARATION OF DIPHENYL-P-STYRYLPHOSPHINE

In a 500 ml round bottom flask equipped with stirrer, reflux condenser, thermometer, and nitrogen by-pass were placed 17.74 g (0.741 mol) of magnesium turnings in a dry nitrogen atmosphere. To this were added 2.7 ml of ethyl bromide dissolved in 10 ml of dry tetrahydrofuran at 31°-53° C. over a period of 15 min. After stirring for an additional hr and subsequent cooling to 5° C., 50 g of p-chlorostyrene, dissolved in 80 ml of dry tetrahydrofuran were added over a period of 70 min with ice cooling at such a rate that the temperature of the soluton never exceeded 23° C. The mixture then was stirred for 1.5 hr at room temperature before being transferred into a dropping funnel inside an inert atmosphere enclosure. This solution then was added in a nitrogen atmosphere to 67.9 g diphenylchlorophosphine dissolved in 250 ml dry tetrahydrofuran at 6°-9° C. over a 30 min. period. The reaction mixture was subsequently stirred at room temperature for 1 hr., cooled to 6° C., and hydrolyzed by adding a solution of 72.5 g ammonium chloride in 500 ml of deaerated water. After separating the organic layer from the aqueous phase and washing the latter with two 250 ml portions of tetrahydrofuran the combined organic solutions were dried over sodium sulfate overnight. After filtration the volume of the solution was reduced to 50% by evaporating the solvent, whereupon heptane was added to precipitate any polymer present. Since no precipitate formed the solution was evaporated to dryness and the remaining viscous oil treated in a nitrogen atmosphere with boiling ethanol. In this manner 30.2 g (34%) of ethanol insoluble material (probably polymer) were obtained whereas from the ethanolic filtrate, after addition of water and cooling, 51.2 g (57.7%) of diphenyl-p-styrylphosphine, mp 77°-78° C., were isolated.

II. PREPARATION OF OXIDIZED STYRYLPHOSPHINE MONOMER

EXAMPLE 10

ATTEMPTED PREPARATION OF $(C_6H_5)_2P(O)N=P(C_6H_5)_2C_6H_4CH=CH_2$

To a stirred solution of diphenyl-p-styrylphosphine (1.0 g, 3.468 mmol) and 0.2 g of 4-t-butylpyrocatechol (a polymerization inhibitor) in tetrahydrofuran (20 ml) under an inert atmosphere was added diphenylphosphinyl azide (0.84 g, 3.468 mmol) in tetrahydrofuran (20 ml) over a period of 1 hr. Nitrogen evolution was observed. Stirring at room temperature was continued for a total of 14 days; since the disappearance of the azido group, as evidenced by infrared spectroscopy, proceeded very slowly. After removal of the solvent, a gummy product indicating the presence of polymeric material, was obtained. The attempted isolation of the monomeric product $(C_6H_5)_2P(O)N=P(C_6H_5)_2C_6H_4CH=CH_2$ was unsuccessful.

EXAMPLE 11

PREPARATION OF $(C_6H_5O)_2P(O)N=P(C_6H_5)_2C_6H_4CH=CH_2$

To a stirred solution of diphenyl-p-styrylphosphine (10.0 g, 34.68 mmol) and 0.2 g of 4-t-butylpyrocatechol (a polymerization inhibitor) in tetrahydrofuran (100 ml) under an inert atmosphere was added a solution of diphenylphosphoryl azide (9.54 g, 34.66 mmol) (which was obtained from Willow Brook Labs., Inc., Waukesha, Wisconsin, and used as received) in tetrahydrofuran (100 ml) over a period of 3 hr; immediate evolution of gas was observed. The solution was then stirred at room temperature for 120 hr. Thereafter, the solvent was removed in vacuo; crystallization from benzeneheptane gave 14.35 g of product (77.3% yield), mp 150°-152° C. Anal. calcd for $C_{32}H_{27}P_2NO_3$: C, 71.77%; H, 5.08%; P, 11.57%; N, 2.62%; O, 8.96%; MW 535.53 Found: C, 71.87; H, 5.35; P, 11.51; N, 2.60, MW 569.

III. BULK POLYMERIZATION OF OXIDIZED STYRYLPHOSPHINE MONOMER

EXAMPLES 12-22

Styrylphosphine monomer oxidized by diphenylphosphorylazide, 2,4-diazido-6-phenyl-s-triazine and 2-azido-4,6-diphenyl-s-triazine (Examples 12-16, 17-18 and 19-22 respectively) were bulk polymerized under the conditions described in Table I below. All of the polymerization reactions were conducted in evacuated ampoules ($10^{-3}$ mm?) in a vacuum line. After completion of each reaction, the residue is each ampoule was extracted with about 10 ml of chloroform, and the soluble polymer was precipitated by treatment of the chloroform solution with heptane, filtered and dried.

Table I

SUMMARY OF BULK POLYMERIZATIONS CONDUCTED ON PRE-OXIDIZED MONOMERS

| Example No. | Monomer Identification | Amt g | Temp °C. | Period h | Yield % | MP °C. | MW |
|---|---|---|---|---|---|---|---|
| 12 | $(\Phi O)_2 P(O)N=P\Phi_2\Phi CH=CH_2$ | 0.41 | 230 | 1.5 | $(90)^a$ | 108–125 | n.a.$^b$ |
| 13 | $(\Phi O)_2 P(O)N=P\Phi_2\Phi CH=CH_2$ | 1.00 | 150 | 1.0 | 76 | 145–162 | 56300 |
| 14 | $(\Phi O)_2 P(O)N=P\Phi_2\Phi CH=CH_2$ | 1.00 | 150 | 5.0 | 74 | 139–156 | 100000 |
| 15 | $(\Phi O)_2 P(O)N=P\Phi_2\Phi CH=CH_2$ | 1.00 | 150 | 24 | 82 | 118–156 | 46200 |
| 16 | $(\Phi O)_2 P(O)N=P\Phi_2\Phi CH=CH_2$ | 15.51 | 165 | 5.0 | 73 (13) | 122–143 | 54500 |
| 17 | $\Phi C_3 N_3[N=P\Phi_2\Phi CH=CH_2]_2$ | 1.00 | 130 | 5.0 | n.r.$^c$ | n.a. | n.a. |
| 18 | $\Phi C_3 N_3[N=P\Phi_2\Phi CH=CH_2]_2$ | 1.00 | 160 | 5.0 | 16 (66) | 195–214 >295 | — — |
| 19 | $\Phi_2 C_3 N_3 N=P\Phi_2\Phi CH=CH_2$ | 1.04 | 190 | 5.0 | 82 | 218–222 | — |
| 20 | $\Phi_2 C_3 N_3 N=P\Phi_2\Phi CH=CH_2$ | 5.00 | 190 | 5.0 | 84 | 215–226 | 6600 |
| 21 | $\Phi_2 C_3 N_3 N=P\Phi_2\Phi CH=CH_2$ | 2.04 | 230 | 0.75 | 90 | 225–240 | 10400 |
| 22 | $\Phi_2 C_3 N_3 N=P\Phi_2\Phi CH=CH_2$ | 0.70 | 230 | 5.0 | 76 | 215–230 | 9500 |

$^a$The number in the parentheses corresponds to the yield of chloroform insoluble polymer.
$^b$Not applicable.
$^c$No reaction.

The results in the Table above show that homopolymers of very good molecular weight characteristics were obtained from the styrylphosphine monomer oxidized with diphenylphosphorylazide. These homopolymers (Exs. 12–16) could readily be formed into molded articles and films.

EXAMPLES 23–28

As shown in Table 2 below, a series of copolymers (Exs. 23–26) and terpolymers (Exs. 27–28) were prepared by the bulk polymerization of the oxidized monomers indicated under the conditions shown. All polymerization reactions were conducted in evacuated ampoules in the manner described for Examples 12–22. The soluble polymer in each example was isolated as also described for Examples 12–22.

Table 2
SUMMARY OF BULK COPOLYMERIZATIONS AND TERPOLYMERIZATIONS

| Ex-ample | Monomer A Identification | Amt g | Monomer B Identification | Amt g | Monomer C Identification | Amt g | Conditions Mole Ratio A:B:C | Temp °C. | Period h | Yield % | Polymer MP °C. | MW | TGA Fig. No. |
|---|---|---|---|---|---|---|---|---|---|---|---|---|---|
| 23 | $(\Phi O)_2P(O)N=P\Phi_2\Phi CH=CH_2$ | 2.00 | $\Phi C_3N_3[N=P\Phi_2\Phi CH=CH_2]_2$ | 0.31 | n.a.[a] | n.a. | 9.2:1.0 | 165 | 5.00 | (82)[b] | >295 | n.d.[c] | 13 |
| 24 | $\Phi P\Phi CH=CH_2$ | 1.03 | $\Phi_2C_3N_3[N=P\Phi_2\Phi CH=CH_2]$ | 2.00 | n.a. | n.a. | 1.0:1.0 | 230 | 0.75 | 80 | 194–104 | 15300 | 14 |
| 25 | $\Phi_2C_3N_3N=P\Phi_2\Phi CH=CH_2$ | 2.07 | $\Phi C_3N_3[N=P\Phi_2\Phi CH=CH_2]_2$ | 0.15 | n.a. | n.a. | 20.4:1.0 | 230 | 1.00 | (48) 50 | >260 206–223 | 4300 | 14 15 |
| 26 | $\Phi_2C_3N_3N=P\Phi_2\Phi CH=CH_2$ | 16.93 | $\Phi C_3N_3[N=P\Phi_2\Phi CH=CH_2]_2$ | 1.23 | n.a. | n.a. | 19.6:1.0 | 230 | 2.0 | (79) 14 | 240–270 187–200 | 3400 | 17 18 |
| 27 | $(\Phi C)_2P(C)N=P\Phi_2\Phi CH=CH_2$ | 2.24 | $\Phi_2C_3N_3N=P\Phi_2\Phi CH=CH_2$ | 0.74 | $\Phi C_3N_3[N=P\Phi_2\Phi CH=CH_2]_2$ | 0.53 | 6.0:2.0:1.0 | 178 | 5.0 | (86) 3 | >295 155–165 | 3900 | 19 — |
| 28 | $(\Phi O)_2P(C)N=P\Phi_2\Phi CH=CH_2$ | 2.00 | $\Phi_2C_3N_3N=P\Phi_2\Phi CH=CH_2$ | 1.10 | $\Phi C_3N_3[N=P\Phi_2\Phi CH=CH_2]_2$ | 0.17 | 6.0:3.3:0.35 | 173 | 5.0 | (87) 5 | >295 115–130 | 20 4800 | — |

[a] Not applicable
[b] The number in the parentheses corresponds to the yield of chloroform insoluble polymer
[c] Not determined

IV. BULK POLYMERIZATION OF DIPHENYL-p-STYRYLPHOSPHINE

EXAMPLES 29–43

Diphenyl-p-styrylphosphine was polymerized by a bulk procedure under the conditions shown in Table 3 below in the quantities shown. All polymerization reactions were conducted in evacuated ampoules either in sealed ampoules (Exs. 29–34) or in ampoules attached to a vacuum line (Exs. 35–43). The polymeric material at the completion of each reaction was extracted with chloroform and isolated in the manner described for Examples 12–22.

TABLE 3
SUMMARY OF BULK POLYMERIZATIONS CONDUCTED ON DIPHENYL-p-STYRYLPHOSPHINE

| Example No. | Monomer g | Conditions Temp. °C. | Period h | Polymer Yield %[a] | MP °C. | MW |
|---|---|---|---|---|---|---|
| 29 | 1.21 | 230 | 0.75 | 69 | 140–165 | 67000 |
| 30 | 0.75 | 230 | 0.75 | 72 | 133–149 | 47000 |
| 31 | 0.76 | 230 | 1.5 | 80 | 130–140 | 28600 |
| 32 | 12.49 | 230 | 1.0 | 81 | 125–146 | 18000 |
| 33 | 1.10 | 230 | 0.3 | 77 | 122–145 | 27000 |
| 34 | 12.15 | 230 | 0.75 | 87 | 127–140 | 31600 |
| 35 | 1.50 | 180 | 0.5 | 73 | 140–148 | 23300 |
| 36 | 2.00 | 210 | 0.5 | 77 | 126–135 | 16400 |
| 37 | 2.00 | 230 | 0.5 | 70 | 128–138 | 11100 |
| 38 | 2.00 | 250 | 0.5 | 58 | 120–136 | 9000 |
| 39 | 2.00 | 100 | 24.0 | 6[b] | 135–145 | 34000 |
| 40 | 2.00 | 100 | 8.0 | 16[b] | 125–135 | 12300 |
| 41 | 2.00 | 100 | 1.0 | 23[c] | 127–135 | 8700 |
| 42 | 2.00[d] | 210 | 0.5 | 65 | 140–150 | 28200 |
| 43 | 2.00 | 210 | 0.5 | 68 | 135–143 | 15200 |

[a]This is the yield of chloroform soluble polymer.
[b]The low yield of the chloroform soluble is due to high gel formation.
[c]The low yield obtained here is due to low conversion of the starting monomer.
[d]This diphenyl p:styrylphosphine was prepared in the absence of the polymerization inhibitor, 4-tert-butylpyrocatechol.

V. PREPARATION OF PHOSPHAZENE GROUP CONTAINING POLYMERS BY OXIDATION OF PREFORMED POLYMERS OF STYRYLPHOSPHINE

The following procedures are representative of those employed for the synthesis of substituted ("oxidized") homopolymers and copolymers shown in Table 4. The styrylphosphine polymers prepared in Examples 29–43 were used in the oxidation reactions.

EXAMPLE 44

PREPARATION OF 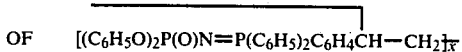

To a stirred solution of polydiphenyl-p-styrylphosphine (2.00 g, 6.936 mmol) in tetrahydrofuran (40 ml) was added diphenylphosphoryl azide (1.91 g, 6,934 mmol) in tetrahydrofuran (40 ml) over a period of 1 hr under an inert atmosphere. Nitrogen gas evolution was observed immediately. The solution was then stirred overnight at room temperature. Subsequently, the polymer was precipitated from solution with heptane (250 ml), filtered and dried in vacuo for 7 hr at 103° C. affording 3.31 g (89% yield) of product, mp 142°–166° C.; MW > 50000.

EXAMPLE 45

PREPARATION OF 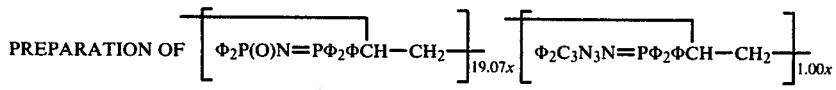

To polydiphenyl-p-styrylphosphine (9.50 g, 32.95 mmol) in tetrahydrofuran (180 ml) was added diphenylphosphinyl azide (7.61 g, 31.29 mmol) in tetrahydrofuran (45 ml) under an inert atmosphere. The resulting solution was stirred at room temperature for 8 days. Subsequently, to the solution was added 2-azido-4,6-diphenyl-s-triazine (0.45 g, 1.64 mmol). After stirring at room temperature for 24 hr the solution was poured onto heptane (500 ml). The precipitated product was filtered and dried in vacuo at 122°–155° C. for 10 hr giving 15.52 g (93% yield) of polymer, mp 198°–222° C.; MW 54600.

EXAMPLES 46–48

The preparation of these examples is not necessary. The results are as shown in Table 4.

EXAMPLE 49
PREPARATION OF CANDIDATE TERPOLYMER

To polydiphenyl-p-styrylphosphine (2.00 g, 6.936 mmol) in tetrahydrofuran (20 ml) was added diphenylphosphoryl azide (1.527 g, 5,549 mmol) in tetrahydrofuran (20 ml) under an inert atmosphere. The resulting solution was stirred at room temperature for 5 days. Then to the solution was added 2-azido-4,6-diphenyl-s-trazine (190 mg, 0.694 mmol). After 2 hr this was followed by 2,4-diazido-6-phenyl-s-triazine (41.3 mg, 0.173 mmol). Subsequently, after stirring for 14 hr at room temperature, an additional quantity of 2-azido-4,6-diphenyl-s-triazine (95.0 mg, 0.347 mmol) was introduced. The resulting solution, following stirring at room temperature for 6 hr, was poured onto heptane (200 ml). The precipitated product was filtered and dried in vacuo at 90°–93° C. for 9 hr giving 3.39 g (93% yield) of polymer, mp 153°–170° C.; MW 91300.

Table 4

HOMOPOLYMERS, COPOLYMERS, AND TERPOLYMERS OBTAINED VIA "OXIDATION" OF PREFORMED POLY(DIPHENYL-p-STYRYLPHOSPHINE)

| Example | Composition | MP °C. | MW | No. Units | TGA FIG. | Starting Material MW | Starting Material No. Units |
|---|---|---|---|---|---|---|---|
| 44 | $[(\Phi O)_2P(O)N=P\Phi_2\Phi CH-CH_2]_x$ | 142–166 | >50000 | 93 | 21 | 11300 | 39 |
| 45 | $[\Phi_2P(O)N=P\Phi_2\Phi CH-CH_2]_{19.07x}[\Phi_2C_3N_3(N=P\Phi_2\Phi CH-CH_2)_2]_{1.00x}$ | 198–222 | 54600 | 102 | 22 | 18000 | 62 |
| 46 | $[\Phi_2P(O)N=P\Phi_2\Phi CH-CH_2]_{6.00x}[\Phi_2C_3N_3(N=P\Phi_2\Phi CH-CH_2)_2]_{1.00x}$ | 240–282 | n.d.[a] | — | 23 | 31600 | 110 |
| 47 | $[\Phi_2P(O)N=P\Phi_2\Phi CH-CH_2]_{8.00x}[\Phi_2C_3N_3(N=P\Phi_2\Phi CH-CH_2)_2]_{2.00x}[\Phi C_3N_3(N=P\Phi_2\Phi CH-CH_2)_2]_{1.00x}$ | 205–220 | 23500 | 46 | 24 | 31600 | 110 |
| 48 | $[\Phi_2P(O)N=P\Phi_2\Phi CH-CH_2]_{8.00x}[\Phi_2C_3N_3(N=P\Phi_2\Phi CH-CH_2)_2]_{1.50x}[\Phi C_3N_3(N=P\Phi_2\Phi CH-CH_2)_2]_{0.25x}$ | 202–215 | n.d. | — | 25 | 31600 | 110 |
| 49 | $[(\Phi O)_2P(O)N=P\Phi_2\Phi CH-CH_2]_{6.00x}[\Phi_2C_3N_3(N=P\Phi_2\Phi CH-CH_2)_2]_{2.00x}[\Phi C_3N_3(N=P\Phi_2\Phi CH-CH_2)_2]_{1.00x}$ | 153–170 | 91300 | 171 | 26 | 31600 | 110 |
| 50 | $[(\Phi O)_2P(O)N=P\Phi_2\Phi CH-CH_2]_{8.00x}[\Phi_2C_3N_3(N=P\Phi_2\Phi CH-CH_2)_2]_{1.50x}[\Phi C_3N_3(N=P\Phi_2\Phi CH-CH_2)_2]_{0.25x}$ | 170–180 | 25800 | 48 | 27 | 15000 | 52 |
| 51 | $[(\Phi O)_2P(O)N=P\Phi_2\Phi CH-CH_2]_{6.00x}[\Phi_2C_3N_3(N=P\Phi_2\Phi CH-CH_2)_2]_{3.50x}[\Phi C_3N_3(N=P\Phi_2\Phi CH-CH_2)_2]_{0.25x}$ | 170–192 | 38000 | 71 | 28 | 16000 | 55 |
| 52 | $[(\Phi O)_2P(O)N=P\Phi_2\Phi CH-CH_2]_{5.00x}[\Phi_2C_3N_3(N=P\Phi_2\Phi CH-CH_2)_2]_{4.00x}[\Phi C_3N_3(N=P\Phi_2\Phi CH-CH_2)_2]_{0.35x}$ | | | | | | |
| | $[(\Phi O)_2P(O)N=P\Phi_2\Phi CH-CH_2]_{6.00x}[\Phi_2C_3N_3(N=P\Phi_2\Phi CH-CH_2)_2]_{3.30x}[\Phi C_3N_3(N=P\Phi_2\Phi CH-CH_2)_2]_{0.35x}$ | 170–215 | 46600 | 87 | 29 | 25750 | 89 |

[a] The molecular weight of this polymer could not be determined due to its insolubility in the solvents tried.

In the formation of the terpolymers (Exs. 46–52) not all of the 2-azido-4,6-diphenyl-s-triazine was added in the second step of the oxidation sequence. This is described in detail above for Example 49. The reason for this was to ensure that when the diazide oxidizing agent was added, that a sufficient number of sites remained to permit interchain linking to take place (scheme I); not intramolecular reaction (scheme II.)

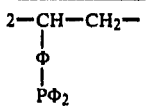

SCHEME I

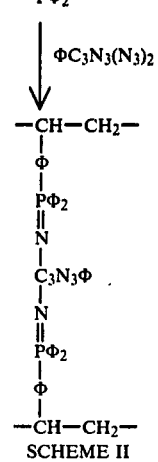

SCHEME II and good processing properties were obtained by oxidation of preformed polystyrylphosphine.

VI. TOXICOLOGICAL TESTING

The toxicological effects of the thermal degradation products of three representative styrylphosphine polymers of the present invention were tested. Samples of polymers of Examples 16, 26 and 45 were formed into 20-27 washers of 0.709 "outside diameter with a center hole of inner diameter 0.25" and 0.08" average thickness. The amounts of materials submitted for testing varied between 9.25 g and 13.10 g. In the test, rats were subjected to thermal degradation products of each polymer material, and no mortalities were observed.

TABLE 5

| Example | Wt. of Polymer Sample (g) | Pyrolysis Temp. °C. | CO Content of Pyrolysis Gas (mg/m$^3$) |
|---|---|---|---|
| 16 | 3.0 g | 500 | 393 (305 ppm) |
|  | 5.34 |  | 174 (174 ppm) |
| 26 | 3.0 | 550 | 348 (270 ppm) |
|  | 5.27 |  | 683 (530 ppm) |
| 45 | 3.0 | 550 | 515 (400 ppm) |
|  | 6.82 |  |  |

VII. MOLDING STUDIES

A number of polymeric compositions as shown in Table 6 below were compressed in a molding device in combination with a Carver Laboratory Press, Model C. All polymer samples in Table 6 below were ground in a mortar before being placed into the mold.

TABLE 6

| Example | Temp. °F. | Contact[a] Time min. | Initial Lead lbs. | Initial Lead Time min. | Final Lead lbs | Final Lead Time min | Remarks |
|---|---|---|---|---|---|---|---|
| 45 | 340 | 10 | 500 | 1 | 1000 | 4 | Very good washers |
| 16 | 260 | 10 | 500 | 1 | 1000 | 4 | Very good washers |
| 26 | 440 | 5 | 500 | 5 | — | — | Acceptable, but brittle washers |
| 44 | 260 | — | 10000 | 0.5 | — | — | Clear film[b] |
| 45 | 270 | 10 | 1000 | 1 | 2000 | 4 | Good washer |
| 18 | 400 | 10 | 500 | 5 |  |  | Opaque, brittle washer |
| 23 | 360 | 10 | 500 | 5 |  |  | Acceptable washer |
| 48 | 440 | 10 | 750 | 5 |  |  | Very good clear washer |
|  | 360 | 10 | 750 | 5 |  |  | Very good clear washer |

[a]The pressure used here was just contact pressure, this operation was performed to bring the sample up to temperature.
[b]In this instance no mold was used, the powdered sample was placed on aluminum plates and was pressed.

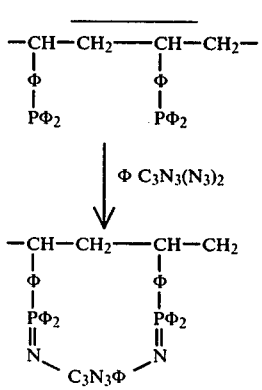

It can be readily determined from the data in Table 4 that terpolymers of very substantial molecular weight

Having now fully described the invention, it will be apparent to one of ordinary skill in the art that many changes and modifications can be made there to without departing from the spirit or scope of the invention as set forth herein.

What is claimed as new and intended to be secured by Letters Patent is:

1. A batch thermal polymerization process for preparing homopolymers, copolymers and terpolymers of oxidized styrylphosphine monomers, which comprises:
polymerizing in batch at a temperature of 130° to 230° C. at least one oxidized styrylphosphine monomer selected from the group consisting of:
$(C_6H_5)_2P(O)N=P(C_6H_5)_2C_6H_4CH=CH_2$,
$(C_6H_5O)_2P(O)N=P(C_6H_5)_2C_6H_4CH=CH_2$,
$(C_6H_5)_2C_3N_3N=P(C_6H_5)_2C_6H_4CH=CH_2$ and
$(C_6H_5)C_3N_3[N=P(C_6H_5)_2C_6H_4CH=CH_2]_2$.

2. The process of claim 1, which further comprises:

homopolymerizing P(O)N=P(C₆H₅)₂C₆H₄CH=CH₂, (C₆H₅O)₂-
(C₆H₅)₂C₃N₃N=P(C₆H₅)₂C₆H₄CH=CH₂ or (C₆H₅)C₃N₃[N=P(C₆H₅)₂C₆H₅CH=CH₂]₂ at a temperature of 130° C. to 230° C. and obtaining a homopolymer product having a molecular weight ranging from 10,000 to 100,000.

3. A homopolymer prepared by the process of claim 1.

4. The homopolymer of claim 3, which has the formula:

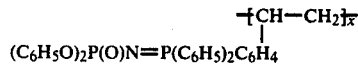

5. A copolymer prepared by polymerizing any two of said oxidized styrylphosphine monomers of claim 1.

6. The copolymer of claim 5, prepared by copolymerizing (C₆H₅)C₃N₃[N=P(C₆H₅)₂C₆H₅CH=CH₂]₂ and (C₆H₅)₂C₃N₃N=P(C₆H₅)₂C₆H₄CH=CH₂ in a mole ratio of 1:20.

7. A copolymer prepared by copolymerizing diphenyl-p-strylphosphine and (C₆H₅)₂C₃N₃N=P(C₆H₅)₂C₆H₄CH=CH₂.

8. The copolymer of claim 7, wherein said reactants are copolymerized in equimolar quantities.

9. A terpolymer prepared by polymerizing any three of said oxidized styrylphosphine monomers of claim 1.

10. The terpolymer of claim 9, which has the formula:

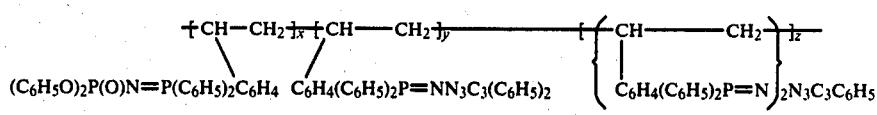

wherein x is 50-90 mole percent, y is 36-15 mole percent and z=10-2 mole percent.

11. The process of claim 1, which further comprises: copolymerizing styrene with at least one oxidized styrylphosphine monomer of claim 1.

12. The process of claim 11 wherein from 20 to 95 mole % styrene is copolymerized with 80 to 5 mole % of at least one of said oxidized styrylphosphine monomers.

13. A copolymer prepared by polymerizing styrene with one of said oxidized styrylphosphine monomers of claim 1.

14. The copolymer of claim 13, which has the formula:

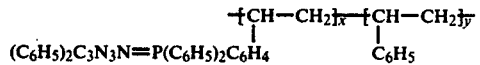

wherein x is a 50-10 mole percent and y is 50-90 mole percent.

15. The copolymer of claim 13, which has the formula:

$$-[CH-CH_2]_x-[CH-CH_2]_y-$$
$$(C_6H_5)_2C_3N_3N=P(C_6H_5)_2C_6H_4 \qquad C_6H_5$$

wherein x is 50-10 mole percent and y is 50-90 mole percent.

* * * * *